United States Patent
Yildiz et al.

(10) Patent No.: US 12,220,514 B2
(45) Date of Patent: Feb. 11, 2025

(54) MULTIPLE PERFUSION CANNULA SYSTEM FOR USE IN AORTIC SURGERY

(71) Applicant: ISTANBUL MEDIPOL UNIVERSITESI, Istanbul (TR)

(72) Inventors: Yahya Yildiz, Istanbul (TR); Murat Ugurlucan, Istanbul (TR); Halil Türkoglu, Istanbul (TR); Korhan Erkanli, Istanbul (TR); Aydin Kahraman, Istanbul (TR); Alper Savas, Istanbul (TR)

( * ) Notice: Subject to any disclaimer, the term of this patent is extended or adjusted under 35 U.S.C. 154(b) by 598 days.

(21) Appl. No.: 17/637,192

(22) PCT Filed: Aug. 21, 2020

(86) PCT No.: PCT/TR2020/050739
§ 371 (c)(1),
(2) Date: Feb. 22, 2022

(87) PCT Pub. No.: WO2021/034293
PCT Pub. Date: Feb. 25, 2021

(65) Prior Publication Data
US 2022/0305184 A1    Sep. 29, 2022

(30) Foreign Application Priority Data
Aug. 22, 2019 (TR) .................. 2019/12633

(51) Int. Cl.
*A61M 1/36* (2006.01)
*A61B 17/12* (2006.01)
(52) U.S. Cl.
CPC ..... *A61M 1/3659* (2014.02); *A61B 17/12109* (2013.01)

(58) Field of Classification Search
CPC ............ A61F 1/3659; A61M 25/0026; A61M 1/3653; A61M 1/3613; A61M 25/0041; A61M 2025/1052; A61M 25/1011; A61M 1/3659; A61M 2025/1097; A61M 60/31; A61B 17/12109
See application file for complete search history.

(56) References Cited

U.S. PATENT DOCUMENTS

| | | | |
|---|---|---|---|
| 5,584,803 A | 12/1996 | Stevens et al. | |
| 5,695,457 A * | 12/1997 | St. Goar | A61M 1/3659 604/509 |
| 5,817,046 A | 10/1998 | Glickman | |
| 6,231,544 B1 | 5/2001 | Tsugita et al. | |
| 6,673,040 B1 * | 1/2004 | Samson | A61B 17/12022 604/509 |

(Continued)

FOREIGN PATENT DOCUMENTS

WO    WO/2001/013983 A2    3/2001

OTHER PUBLICATIONS

International Search Report for corresponding PCT/TR2020/050739 dated Jul. 6, 2021.

(Continued)

*Primary Examiner* — Sarah Al Hashimi
*Assistant Examiner* — Meagan Ngo
(74) *Attorney, Agent, or Firm* — Egbert, McDaniel & Swartz, PLLC

(57) ABSTRACT

Disclosed are multiple perfusion cannulas that can be used for the prevention of complications due to hypoperfusion particularly in aortic surgery.

12 Claims, 1 Drawing Sheet

(56) References Cited

U.S. PATENT DOCUMENTS

| | | | | |
|---|---|---|---|---|
| 6,702,773 B1* | 3/2004 | Macoviak | ............ | A61M 1/3613 |
| | | | | 604/4.01 |
| 2002/0169437 A1* | 11/2002 | Macoviak | ......... | A61M 25/0067 |
| | | | | 604/102.03 |
| 2003/0236496 A1* | 12/2003 | Samson | ............ | A61B 17/12045 |
| | | | | 604/103.02 |
| 2005/0004503 A1* | 1/2005 | Samson | .................. | A61M 5/44 |
| | | | | 604/6.14 |
| 2006/0200191 A1 | 9/2006 | Zadno-Azizi | | |
| 2013/0281761 A1* | 10/2013 | Kapur | ................. | A61M 60/531 |
| | | | | 600/16 |
| 2014/0276399 A1* | 9/2014 | Bian | ..................... | A61M 25/10 |
| | | | | 604/284 |
| 2016/0158506 A1* | 6/2016 | Eliasen | ............... | A61M 1/3659 |
| | | | | 604/509 |
| 2018/0289464 A1* | 10/2018 | Kassab | .................... | A61B 5/01 |
| 2019/0167954 A1* | 6/2019 | Zhadkevich | ..... | A61B 17/12045 |

OTHER PUBLICATIONS

Written Opinion of the International Searching Authority for corresponding PCT/TR2020/050739 dated Jul. 6, 2021.

* cited by examiner

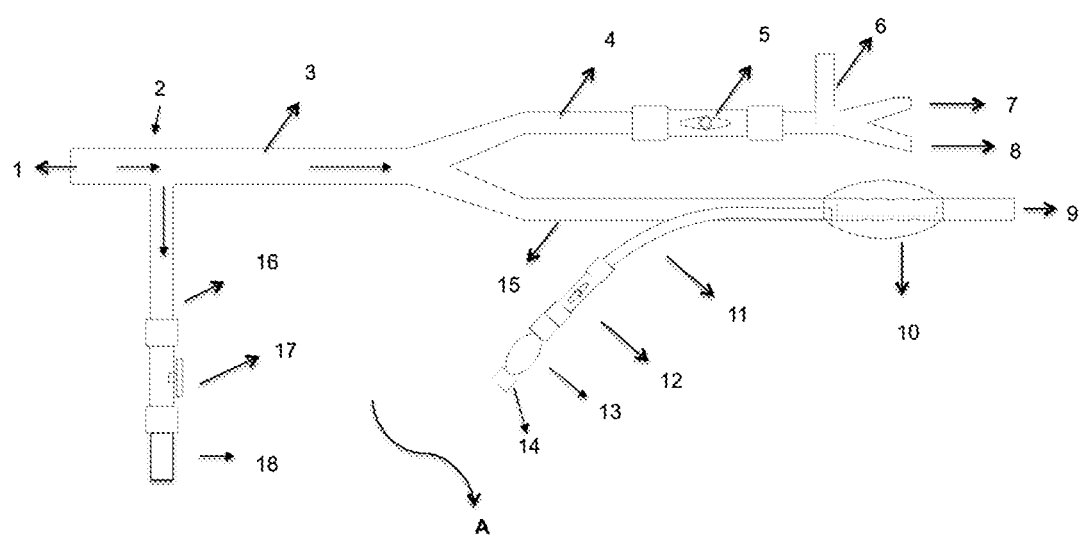

MULTIPLE PERFUSION CANNULA SYSTEM FOR USE IN AORTIC SURGERY

TECHNICAL FIELD

This invention refers to multi vessel perfusion cannulas that can be used for the prevention of complications due to total circulatory arrest particularly during in aortic surgery.

PRIOR ART

Aortic arch replacement operations can only be performed by applying total circulatory arrest, which means interrupting blood flow to the entire body or completely disrupting blood flow to the entire body for a certain period of time. Interruption of blood flow to organs during the operation, especially when the operation lasts for extended periods, leads to complications due to the lack of blood supply to organs. Especially in cases where there is poor blood flow or no blood flow to the brain, loss of brain functions may occur at different levels while the poor blood flow to any other organ such as kidneys cause conditions that lead to substantial and permanent damage including organ failure.

The prior art comprises exclusively cerebral perfusion cannulas, which are used in aortic surgery. Commercially available perfusion cannulas are in the form of a single cannula, and they are inserted in a single artery such as the aorta, the axillary artery or the femoral artery; this cannula provides blood flow to the entire body by a heart-lung machine when the heart is stopped during aortic surgery. When existing cannulas are used in the surgical treatment of aneurysms or ruptures involving the aortic arch, total circulatory arrest method in which the patient is cooled down to very low to very low temperatures and the entire circulation is stopped. Unfortunately, this method is likely to produce complications especially in prolonged operations.

In other words, in major vascular surgery, the body is cooled down and the circulation is stopped to protect the organs. There is another surgical method where a cannula is inserted in a main artery to the brain to supply blood to the brain in order to maintain brain functions for as long as the circulation is stopped. Referred to as selective cerebral perfusion, this method may cause cerebral deficit that is brain damage, if insufficiency involving the vertebrobasilar system or Willis polygon is present.

Even assuming there is no insufficiency involving the vertebrobasilar system or Willis polygon, this method of protection may cause multiple organ damage apart from the brain depending on the amount of cooling and duration of the circulatory arrest. Such cases involve a high rate of morbidity and mortality.

Studies report that, after such operations, permanent neurological damage is 6%, temporary neurological damage is 7%, 30-day mortality rate is 7% and 5-year mortality year is 23% (1). Even the mortality rate in aortic surgery is 5%, which could be considered high (2).

As indicated in the prior art, in cases where the entire circulatory system is to be disrupted, namely during the surgical treatment of the aneurysm of the aortic arch, cannulas are needed that will allow the maintenance of uninterrupted blood flow to the entire body including the heart in order to prevent organ ischemia.

BRIEF DESCRIPTION OF THE INVENTION

The invention refers to a multiple perfusion cannula (A) suitable for use in order to maintain blood flow to the entire body in surgical operations requiring disruption of blood flow in the body, namely the operations to be performed along the entire aorta. (FIG. 1).

The perfusion cannula (A) that is the subject of the invention provides connection to the heart-lung machine by means of the aorta outlet (1) located on it, and the blood from this outlet enters through the main cannula (3) and from the upper extremity feed compartment (4) the blood is distributed to innominate artery (truncus brachiocephalicus), the left main carotid artery and the left subclavian artery as well as to the descending aorta from the lower extremity feed compartment (15) and to the ascending aorta by means of the coronary perfusion cannula (16). This way, blood flow is maintained in the entire body in surgical operations on the ascending, arch and descending aorta.

Multiple perfusion cannula (A) that is the subject of the invention will help prevent complications including neurological problems due to hypothermia and hypoperfusion as well as liver and renal failure, gastrointestinal ischemia and myocardial ischemia without having to cool the patients or disrupt the entire circulatory system. If necessary, the coronary perfusion compartment can be aborted, ensuring heart protection by administration of cardioplegia.

BRIEF DESCRIPTION OF THE FIGURE

A representative drawing of the multiple perfusion cannula (A) that is the subject of the invention is provided in FIG. 1.

Reference numbers in the FIGURES and the corresponding parts are listed below;

1: Aorta Outlet
2: Blood Flow Direction
3: Main Cannula
4: Feed Compartment at the upper extremity
5: Feed Compartment Clip at the upper extremity
6: Innominate Artery Cannula
7: Left Carotid Artery Connection
8: Left Subclavian Artery Connection
9: Descending Aorta Outlet
10: Descending Aorta Balloon
11: Pilot Balloon Connection
12: Pilot Balloon Connection Clip
13: Pilot Balloon
14: Pilot Balloon Inflating Nozzle
15: Lower Extremity Feed Compartment
16: Ascending Aorta or Coronary Perfusion Cannula (or Aortic Root Cannula)
17: Ascending Aorta Perfusion Cannula Clip
18: Coronary Feed Cannula End

DETAILED DESCRIPTION OF THE INVENTION

The multiple perfusion cannula (A) that is the subject of the invention comprises the main cannula (3) and the ascending aorta cannula (16) branching from the main cannula (3), upper extremity feed compartment (4) and lower extremity feed compartment (15).

The aorta outlet (1) located on the main cannula (3) connects the multiple perfusion cannula (A) that is the subject of the invention to the heart-lung machine.

The coronary perfusion cannula (16) located on the main cannula (3) is the cannula placed on the ascending aorta by purse-string suture and which provides blood flow to the coronary arteries and blood supply to the heart even when the ascending aorta is clamped. The air inside the cannula can be discharged before use by means of the ascending aorta perfusion cannula clip (17) located on the coronary perfusion cannula (16) The coronary perfusion cannula (16) provides blood flow to the coronary arteries via the coronary feed cannula end (18) located on it.

For the purposes of this invention, the terms "coronary perfusion cannula (16)", "ascending aorta cannula (16)" or "aortic root cannula (16)" are synonymous and can be used interchangeably.

If the surgical operation must be performed by stopping the heart, the heart can be protected by means of administering cardioplegia.

The upper extremity feed compartment (4) located on the main cannula (3) comprises the left main carotid artery connection (7), the left subclavian artery connection (8) and the innominate artery cannula (6). The left main carotid artery connection (7) and the left subclavian artery connection (8) are directed into both carotid arteries by means of the purse string sutures applied to the ascending aorta and via the ascending aorta and supply blood to the brain. The innominate artery cannula (6) located on the upper extremity feed compartment (4) provides blood supply to the upper right part of the body (the right arm, the right part of the neck and the right part of the head).

The clips located on the cannulas can be used to discharge the air inside the cannula or monitor the blood flow inside the cannula. The air inside the cannula can be discharged before use by means of the upper extremity feed compartment clip (5) on the upper extremity feed compartment (4) located on the main cannula (3).

The lower extremity feed compartment (15) located on the main cannula (3) has a balloon inflating nozzle (hose or connection) (12), which connects to lower extremity feed compartment (15) via the pilot balloon connection (11) and is used to inflated the descending aorta balloon (10) located here.

When the descending aorta balloon (10) located on the lower extremity feed compartment (15) located on the main cannula (3) is inflated, it prevents the blood from the descending aorta from flowing to the surgical site. The lower extremity feed compartment (15) located on the main cannula (3) that is the subject of the invention is the cannula that feeds the entire lower half of the body including the kidneys, the liver, the gastrointestinal system and both lower extremities.

The pilot balloon connection clip (12) on the lower extremity feed compartment (15) located on the main cannula (3) can be used to discharge the air inside the cannula before use.

For the purpose of this invention, the term "clip" refers to any assembly that enables the cannula line to be turned on and off as needed or enables the air built up inside or the body fluids to be discharged. The upper extremity feed compartment clip (5), the pilot balloon connection clip (12) and the ascending aorta perfusion cannula clip (17) that are the subject of the invention can be in the form of a tap, button, valve or any other assembly of the same function.

In a preferred application of the invention, clips are used in the form of valves and the blood flow can be completely switched off or the flow rate can be adjusted as needed when the valve is rotated a quarter turn or 2 complete turns.

The upper extremity feed compartment clip (5), the pilot balloon connection clip (12) and the ascending aorta perfusion cannula clip (17) located on the cannula (A) that is the subject of the invention also comprise a pressure controller.

The pilot balloon connection (11) located on the multiple perfusion cannula (A) that is the subject of the invention comprises a pilot balloon (13) and a pilot balloon inflating nozzle (14). The liquid flow supplied at this point is conveyed to the balloon (10) located on the lower extremity feed compartment (15) via the pilot balloon connection clip (12) located on the pilot balloon connection (11). In other words, the balloon is inflated with the liquid. During the application, while the balloon (10) is inside the body of the patient not visible to the user, the pilot balloon (13) can be seen by the user, which enables the user to know how much the balloon inside the body (10) is inflated without having to see the balloon (13). Similarly, the liquid that builds up in the pilot balloon (13) and the balloon (10) located inside the body of the patient during the application is removed by means of discharging the liquid inside the balloon via the pilot balloon inflating nozzle (14) and the pilot balloon (13) and the balloon (10) are deflated. In other words, while the balloon (10) is inflated by delivering liquid via the pilot balloon inflating nozzle (14), the pilot balloon (13) can be monitored and the artery can be safely closed by means of the balloon (10).

The multiple perfusion cannula (A) that is the subject of the invention can be made of any material compatible with the physiological environment and known to be usable in surgical conditions. In a preferred application of the invention, the multiple perfusion cannula (A) that is the subject of the invention can be made of a material selected from among a group comprising polyurethane (PU), polyvinyl chloride (PVC), silicone, and metal wire reinforced silicone.

In a preferred application of the invention, at least one of the components of the multiple perfusion cannula (A), which are the main cannula (3), the aortic root cannula (16), the descending aorta balloon (10), the left carotid artery connection (7), the left subclavian artery connection (8) the upper extremity compartment (4), the lower extremity compartment (15) may comprise strips made of radiopaque material. The objective of equipping the cannula with a radiopaque strip is to be able to perform radiological examination in case a part of the cannula is accidentally left inside the patient's body after surgery.

The multiple perfusion cannula (A) that is the subject of the invention is connected to the heart-lung machine via the aorta outlet (13) located on the main cannula (3) and provides blood flow into the cannula. The blood that flows into the cannula (A) passes through the innominate artery cannula (6), the left main carotid artery connection (7) and the left subclavian artery connection (8) and is directed to the innominate artery, the left main carotid artery and the left subclavian artery to feed the brain.

Similarly, the blood that flows into the cannula passes through the lower extremity compartment (15) and the balloon (10) and connects to the body via the descending aorta outlet (9) being delivered to the kidneys, the liver, the gastrointestinal system and both lower extremities while at the same time it passes through the ascending aorta and the coronary perfusion cannula (16) and is delivered to the coronary arteries, thereby maintaining blood flow.

In another aspect, the invention refers to a cannulation kit characterized in that it comprises;
  multiple perfusion cannula comprising the main cannula (3) and the ascending aorta cannula (16) located on the main cannula (3), the upper extremity feed compartment (4) comprising the innominate artery cannula (6), the left main carotid artery connection (7) and the left subclavian artery connection (8) and the lower extremity feed compartment (15) comprising the descending aorta balloon (10)
  a dilator that can pass through the cannula (A), a guidewire, at least one lancet, at least one injector.

For the purposes of this description, the term "comprise" is intended to mean "include".

Wherever technically possible, the application of the invention can be combined.

Applications are described here, in a manner to comprise specific features/components.

The description also essentially covers the applications comprising said features/components or applications made up thereof.

Applications specifically and expressly described here may, solely or in conjunction with one or more other applications, constitute the basis of a waiver.

REFERENCES

1. Zierer A, El-Sayed Ahmad A, Papadopoulos N, et. al. Fifteen years of surgery for acute type A aortic dissection in moderate-to-mild systemic hypothermia. *Eur J Cardiothorac Surg.* 2017 January; 51(1):97-103. doi: 10.1093/ejcts/ezw289. Epub 2016 Oct. 2.
2. Urgnani F1, Lerut P, Da Rocha M, et. al. Endovascular treatment of acute traumatic thoracic aortic injuries: a retrospective analysis of 20 cases. *J Thorac Cardiovasc Surg.* 2009 November; 138(5):1129-38. doi: 10.1016/j.jtcvs.2008.10.057. Epub 2009 Jun. 13.

The invention claimed is:

1. A multiple perfusion cannula for use in aortic surgery, comprising: a main cannula, an upper extremity feed compartment located on the main cannula comprising an innominate artery cannula, a left main carotid artery connection and a left subclavian artery connection, a lower extremity feed compartment comprising a descending aorta balloon and an ascending aorta cannula.

2. A multiple perfusion cannula according to claim 1, wherein the main cannula comprises an aorta outlet connecting the cannula to a heart-lung machine.

3. A multiple perfusion cannula according to claim 2, comprising, on a coronary perfusion canulla, a coronary feed cannula end and an ascending aorta perfusion cannula clip that can be used to discharge air inside the cannula before use.

4. A multiple perfusion cannula according to claim 3, comprising an upper extremity feed compartment clip located on the upper extremity feed compartment.

5. A multiple perfusion cannula according to claim 4, comprising a pilot balloon connection on the lower extremity feed compartment.

6. A multiple perfusion cannula according to claim 5, wherein a pilot balloon, a pilot balloon connection clip and a balloon inflating nozzle are located on the pilot balloon connection.

7. A multiple perfusion cannula according to claim 5, comprising a pilot balloon connection clip on the lower extremity feed compartment.

8. A multiple perfusion cannula according to claim 7, wherein the upper extremity feed compartment clip, the pilot balloon connection clip and the ascending aorta perfusion cannula clip located on the cannula also comprises an pressure controller.

9. A multiple perfusion cannula according to claim 8, wherein the cannula is made of a material compatible with the physiological environment and known to be usable in surgical conditions.

10. A perfusion cannula according to claim 9, wherein the cannula is made of a material selected from among a group consisting of polyurethane, polyvinyl chloride, silicone, and metal wire reinforced silicone.

11. A perfusion cannula according to claim 1, wherein at least one of the main cannula, the aortic root cannula, the descending aorta balloon, the left carotid artery connection, the left subclavian artery connection, the innominate artery cannula, the upper extremity compartment, and the lower extremity compartment comprise strips made of radiopaque material.

12. A cannulation kit comprising:

a multiple perfusion cannula comprising a main cannula and an ascending aorta cannula located on the main cannula, an upper extremity feed compartment comprising an innominate artery cannula, a left main carotid artery connection a and a left subclavian artery connection a and a lower extremity feed compartment comprising a descending aorta balloon;

a dilator which can fit inside the cannula, a guidewire, at least one lancet, and at least one injector.

* * * * *